(12) United States Patent
Froud et al.

(10) Patent No.: US 6,565,801 B1
(45) Date of Patent: May 20, 2003

(54) ODOR CONTROL APPARATUS (75) Inventors: David Froud, Kent (GB); Colin D. Froud, Kent (GB)

(73) Assignee: CSO Technik Limited, Kent (GB)

( * ) Notice: Subject to any disclaimer, the term of this patent is extended or adjusted under 35 U.S.C. 154(b) by 0 days.

(21) Appl. No.: 09/414,522

(22) Filed: Oct. 8, 1999

(30) Foreign Application Priority Data

Oct. 8, 1998 (GB) .............................................. 9822011

(51) Int. Cl.$^7$ ................................................. A61L 9/22

(52) U.S. Cl. ............................ 422/5; 422/292; 210/205

(58) Field of Search ............................ 422/5, 28, 292, 422/300, 123; 298/7, 309; 4/662; 414/292; 210/205, 218

(56) References Cited

U.S. PATENT DOCUMENTS

| 3,772,712 | A | * | 11/1973 | Renn et al. ..................... 4/142 |
| 3,857,934 | A | * | 12/1974 | Bernstein et al. .............. 424/30 |
| 3,995,754 | A | * | 12/1976 | DeKoning ............... 214/83.26 |
| 4,571,752 | A | * | 2/1986 | Bick ............................. 4/300 |
| 4,819,276 | A | * | 4/1989 | Stevens ......................... 4/233 |
| 5,072,850 | A | * | 12/1991 | Gagnon et al. ............. 220/300 |
| 5,181,393 | A | * | 1/1993 | Lott .............................. 62/264 |
| 5,240,484 | A | * | 8/1993 | Genovese et al. ............ 55/279 |
| 5,445,397 | A | * | 8/1995 | Evans ..................... 280/47.18 |
| 5,636,593 | A | * | 6/1997 | Vito ............................ 119/165 |

* cited by examiner

Primary Examiner—Robert J. Warden, Sr.
Assistant Examiner—Sean E. Conley
(74) Attorney, Agent, or Firm—Clark & Brody (57) ABSTRACT

Odor control apparatus comprising a container for containing solid malodorous material, and inlet means for feeding deodorizing gaseous material over the solid malodorous material contained in the container.

20 Claims, 7 Drawing Sheets

ODOR CONTROL APPARATUS

The present invention relates to odour control apparatus comprising a container for containing solid malodorous material, especially, but not exclusively, grit recovered from sewage effluent.

Such grit is recovered from detritus and other grit removing machinery and is fed into a skip via a chute. Whilst in the skip, bioactive micro-organisms are able to break down the toxic materials, and odorous gaseous material thus released is oxidised by the surrounding air. However, during this process, the skip contents rapidly become malodorous and offensive to the neighbouring community.

The present invention seeks to provide a remedy.

Accordingly, the present invention is directed to odour control apparatus comprising a container for containing solid malodorous material, and inlet means for feeding deodorising gaseous material over the solid malodorous material contained in the container.

The container may be open at its top, and a cover may extend over the top of the container and so create a barrier between regions over the solid malodorous material and the surrounding air.

The cover may comprise sheet material in the form of a plurality of segments to enable the cover to be extended over the container to cover it and retracted to provide access to the container.

The segments may overlap one another when the cover is retracted, but substantially less so, or not at all, when the cover is extended.

The segments may be provided with lips to act as abutment stops defining the limits to, which adjacent segments can be moved relative to one another in the cover-extending direction, and in the cover-retracting direction.

The cover may be in the form of a conch.

The cover may alternatively comprise flexible sheet material. It may be antistatic and/or water-resistant and/or air-breathable.

The apparatus may further comprise support means. These may support the sheet material in such a manner that it is slanted so that rainwater runs off it more easily than if it were horizontal.

The said inlet means may be provided in the said support means. The latter may also be provided with a chute to enable grit or other solid malodorous material to be poured into the container whilst the cover remains in place.

The container may be in the form of a skip.

The support means may comprise a backboard.

The deodorising gaseous material may comprise ionised air.

The cover may be provided with a drawable hem. Alternatively or in addition, the hem of the cover may be elasticated. Either way, a single operative can easily remove the cover to allow access to and removal of the full skip. This can then be replaced by an empty skip and the cover can then be lifted over the empty skip and the process repeated.

The present invention extends to a method of treating solid malodorous material comprising placing the latter in a container and passing deodorising gaseous material over it whilst it remains in the container.

In a further aspect of the present invention, there is provided a cover comprising rigid sheet material in the form of a plurality of segments to enable the cover to be extended over an article to cover it and retracted to provide access to the article, in which the segments overlap one another when the cover is retracted and do not overlap one another, or overlap one another substantially less when the cover is extended.

Examples of apparatus embodying the present invention are shown in the accompanying drawings, in which.

Figure 1:
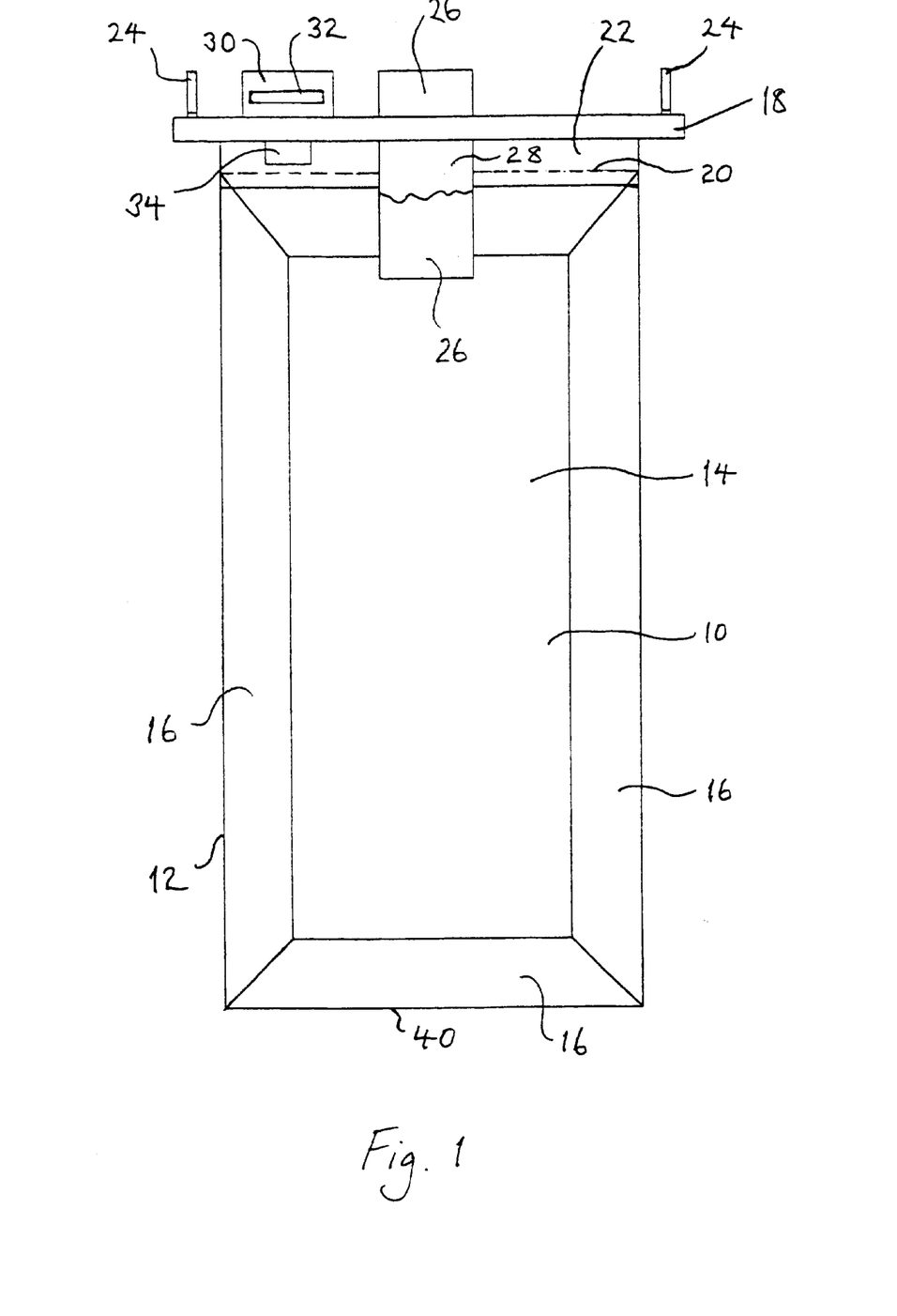
FIG. 1 shows a plan view of the apparatus with a cover thereof removed to show other parts of the apparatus more clearly.
Figure 2:
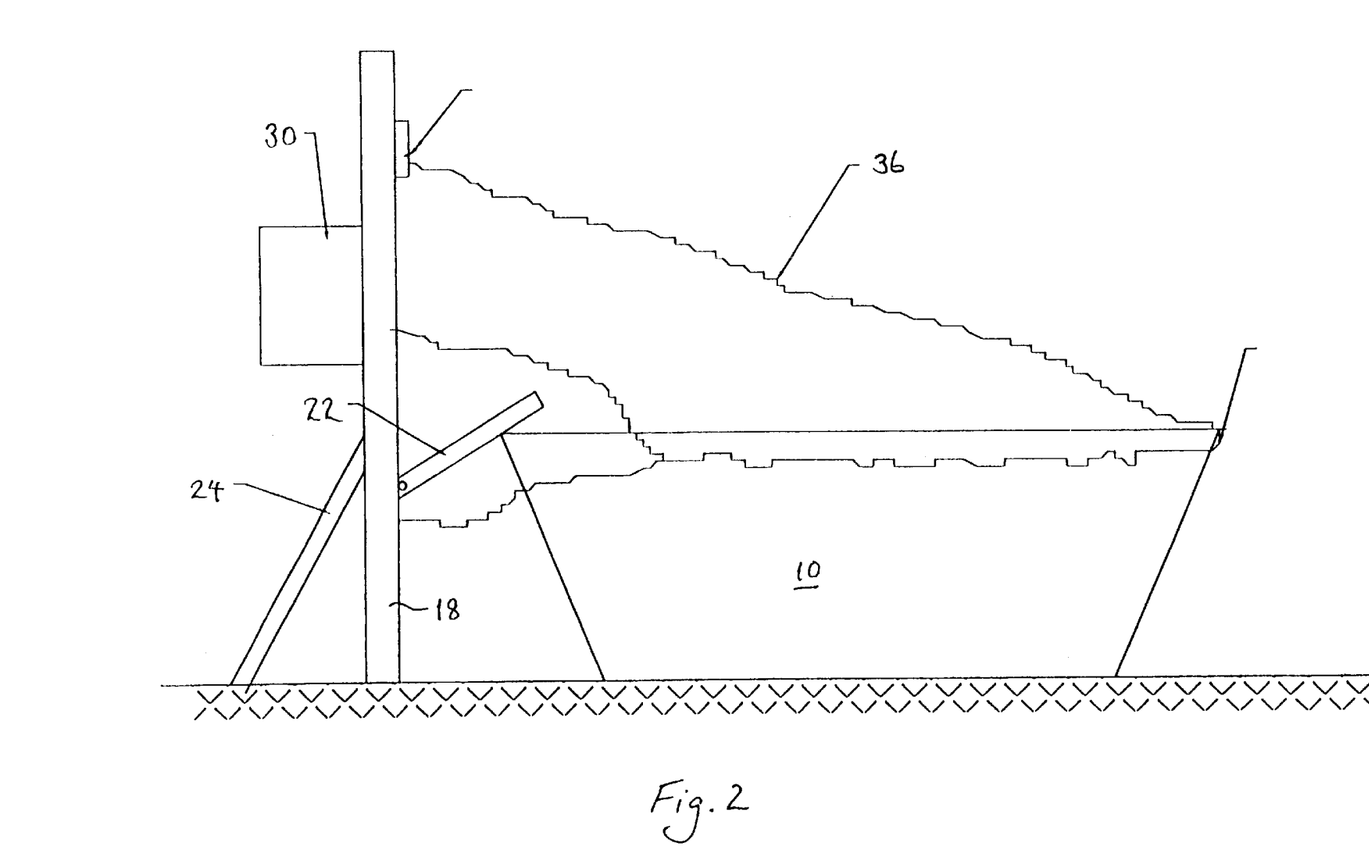
FIG. 2 shows an elevational side view of the apparatus with the cover appearing to be transparent for illustrative purposes.
Figure 3:
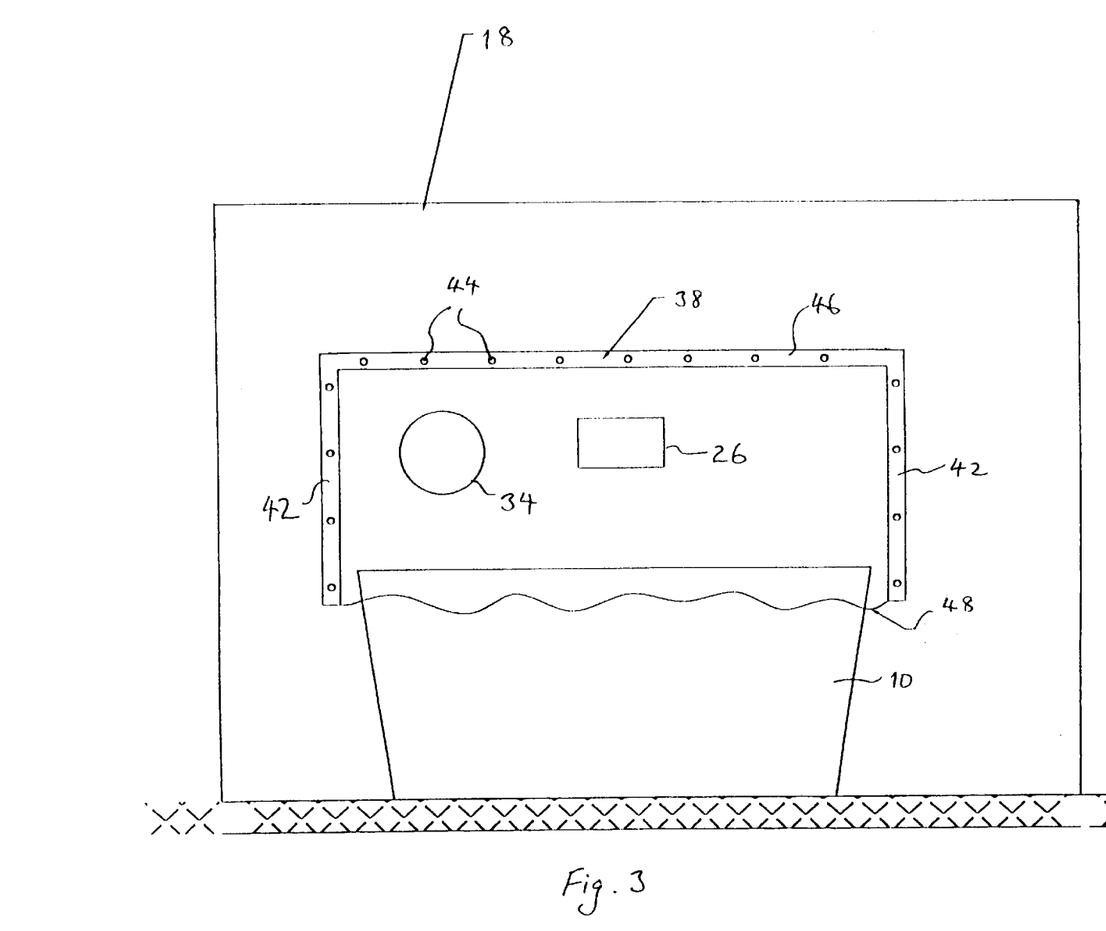
FIG. 3 shows an end view of the apparatus with the cover thereof removed to show other parts of the apparatus more readily.
Figure 4:
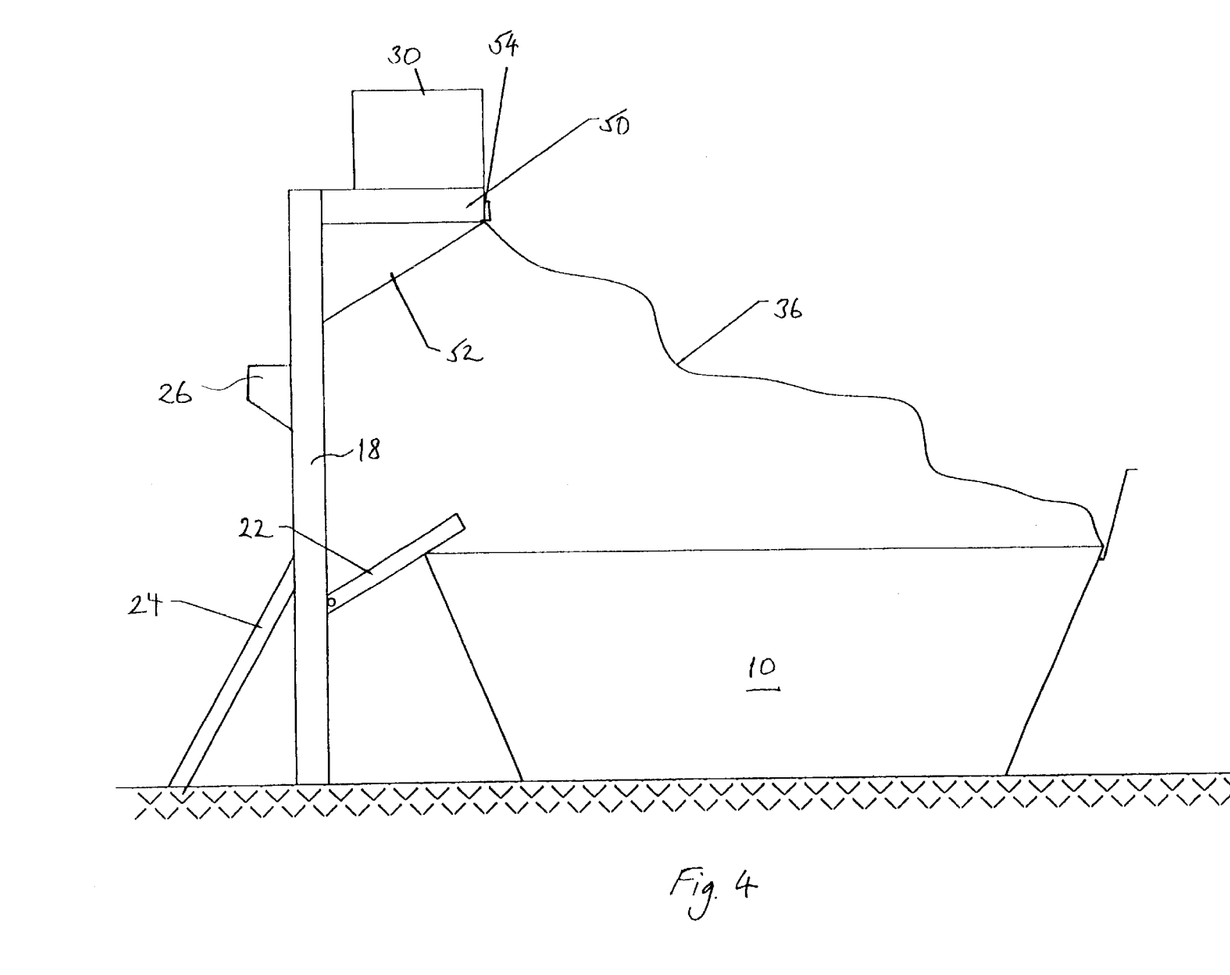
FIG. 4 shows an elevational side view of a modified form of the apparatus.

The apparatus shown in FIGS. 1 to 3 comprise a skip 10 which has an open top defined by a rim 12. The skip 10 also has a bottom wall 14 which is of smaller area than that defined by the rim 12, and four side walls 16 slanting inwardly in a downward direction. An upright backboard 18 is positioned adjacent to one end 20 of the skip 10 and is wider than the width of the skip 10 and substantially higher than the height thereof. A flexible sealing plate 22 is secured to the backboard 18 and bridges the gap between the skip end 20 and the backboard 18. This sealing board has substantially the same width as the skip 10. The backboard 18 is supported in its upright position, on the ground or other surface on which the skip rests, by means of struts 24.

A chute 26 extends from the side of the backboard 18 which is further from the skip 10, through an aperture in the backboard 18, to the side on which is located the skip, the lower end of the chute 26 projecting over the skip interior. A flap 28 acts as a barrier to air passing from the skip interior to the surrounding air but at the same time will readily yield to any incoming grit.

A blower 30 is attached to the rear side of the backboard 18 and is provided with an ioniser 32. An inlet 34 extends from this blower 30 through a further aperture in the backboard 18 to a position over the skip interior.

A tailored cover 36 made of sheet material extends from every point along a line 38, itself extending across the greater part of the width of the backboard 18 close to the top thereof, down to the end 40 of the skip which is further from the backboard 18. The cover also extends from every point along respective lines 42 which extend downwardly from the first line to positions immediately adjacent to the rim 12 of the skip 10, and forwardly from those lines to the end 40 of the skip. The cover is secured to the backboard 18 along the said lines by means of turn-buckles 44 and Velcro (Trade Mark) 46 to form an effective seal between the backboard 18 and the cover 36. The cover 36 also has a hem 48 which extends around and just below the rim 12 of the skip 10. This hem may be gathered and/or elasticated to enable it to fit snugly under the rim 12 of the skip 10. In this way, the cover 36 forms an effective barrier between regions over the container interior where solid malodorous material is to be dumped, and the surrounding air. These regions include the lower end of the chute 26 as well as the inlet 34.

The sheet material of the cover 36 is light in weight to enable one operative to remove and replace it, yet strong enough to resist wind loads. It is preferably anti-static and water-resistant. It may also be air-breathable. A pulley system (not shown) may be provided to assist in the removal and replacement of the cover 36.

When the apparatus is in use with the parts arranged as shown in FIG. 2, malodorous grit from sewage effluent is deposited into the skip 10 via the chute 26 from a position on the side of the backboard 18 further from the skip 10. This is done with the cover 36 in place sealed by the turn-buckles and Velcro (Trade Mark).

The blower 30 is switched on as well as the ioniser 32 within so that ionised air passes over the surface of the grit within the skip 10. This oxidises the gaseous material released by the contents of the skip 10 so as to deodorise that gaseous material.

When the grit is ready for transportation away from the site, the cover 36 is readily removed from the skip enabling the latter to be readily hoisted on to a skip removal vehicle, whereafter an empty skip is placed in the same position as the one that has been carried away, the cover 26 is placed over it in the same way as shown in FIG. 2, and the whole process described with reference to the first skip is repeated. All this can be effected whilst the blower 30 and/or the ioniser 32 remains switched on.

Figure 5:
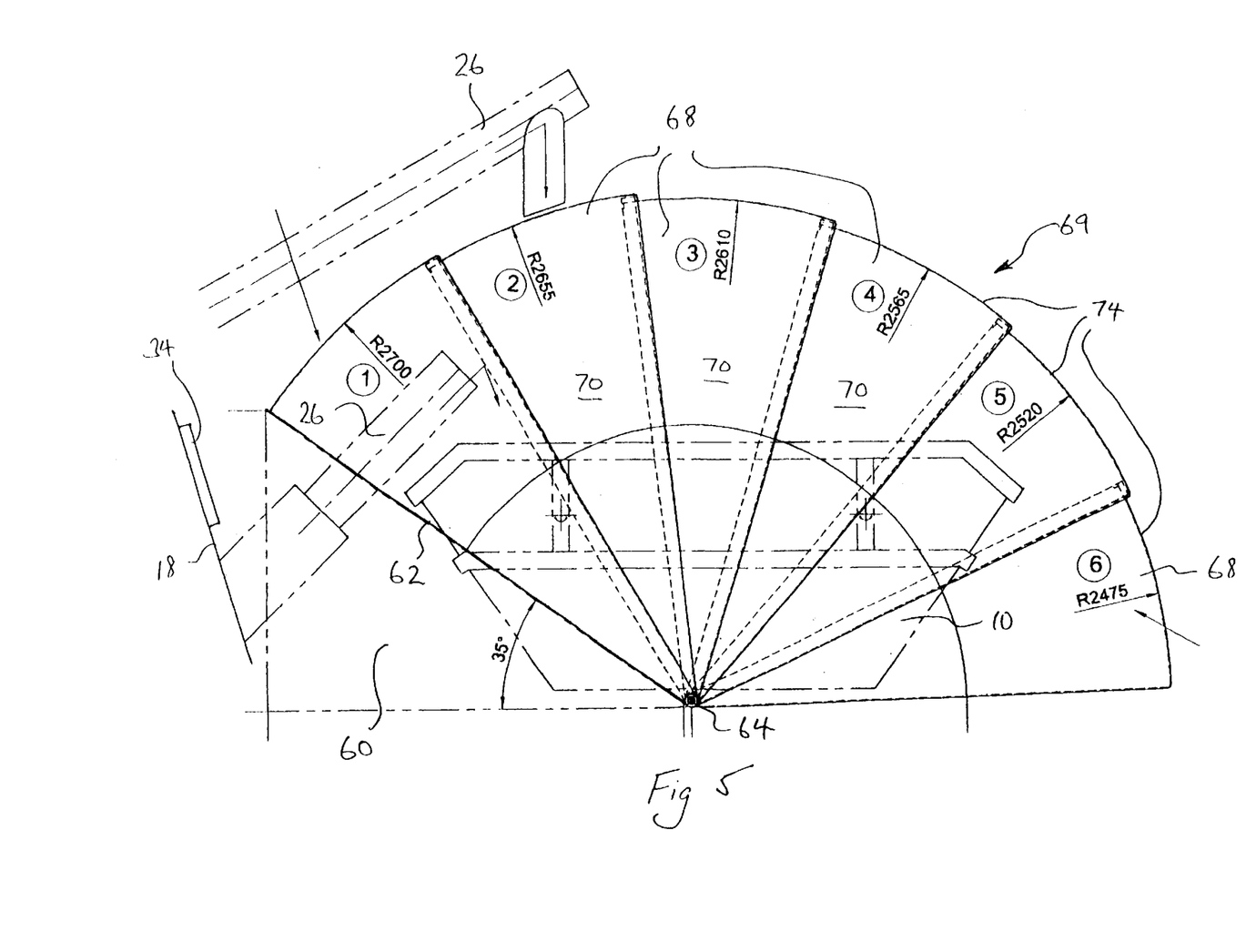
FIG. 5 shows a side elevational view of a modified form of apparatus made in accordance with the present invention.
Figure 6:
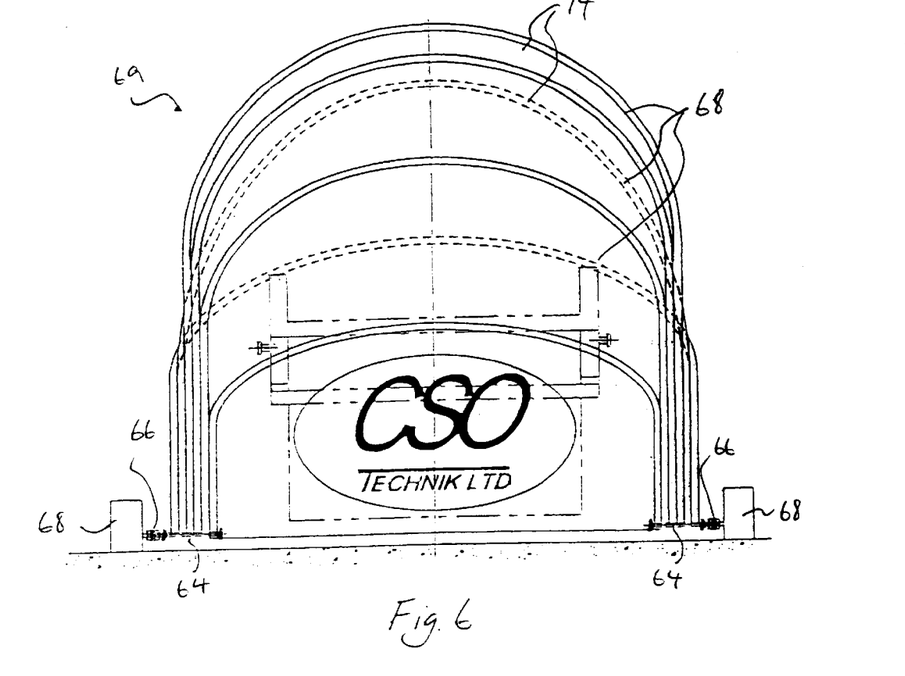
FIG. 6 shows a front elevational view of the apparatus shown in FIG. 5.

In the modified apparatus shown in FIGS. 5 to 9, the chute 26 extends in an upward slanting direction from the board 18 to a position just above one end of the skip 10. Extending forwardly from the board 18 on opposite sides of the skip 18 are two fixed walls 60 (only one of which is shown in FIG. 5), each of which has a slanting upper top surface 62 which is inclined downwardly in a forward direction at an angle of substantially 35° to the horizontal.

At the forward end of each side all 60, where the incline 62 meets the ground, there is located a rotary mounting shaft 64 coupled via a motor coupling 66 to a motor 68 which is thus arranged to rotate the shaft 64 in a controlled fashion. A series of six rigid sheet segments 68, which together constitute a cover 69 of a skip 10, each having generally acute triangular side portions 70 with their acute angles being at the shaft 64 where that portion is coupled to the shaft via a rotary bearing 72, and a part-spherical portion 74 interconnecting the triangular side portions 70.

Figure 7:
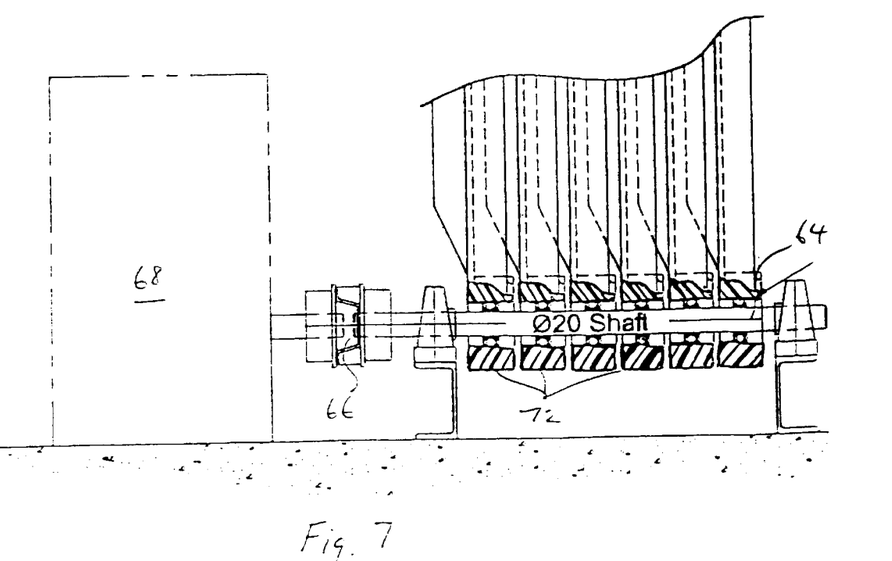
FIG. 7 shows a front elevational view on a larger scale of parts of the apparatus shown in FIGS. 5 and 6 with the cover thereof in a retracted position.
Figure 8:
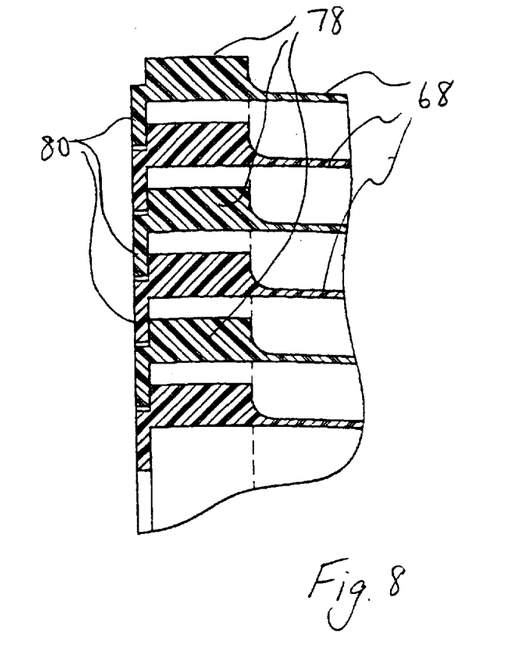
FIG. 8 shows a cross-sectional view through parts of the apparatus shown in FIGS. 6 and 7 with the cover in a retracted position.

In the retracted condition of the cover 69 shown in FIG. 7, the series of six segments 68 are nestled one within another, so that they overlap one another, with the outermost segment having its side portions secured respectively to the inclines 62 of the walls 60.

When it is in its extended position, as shown in FIG. 5, the cover 69 is formed as a conch over the skip 10.

Figure 9:
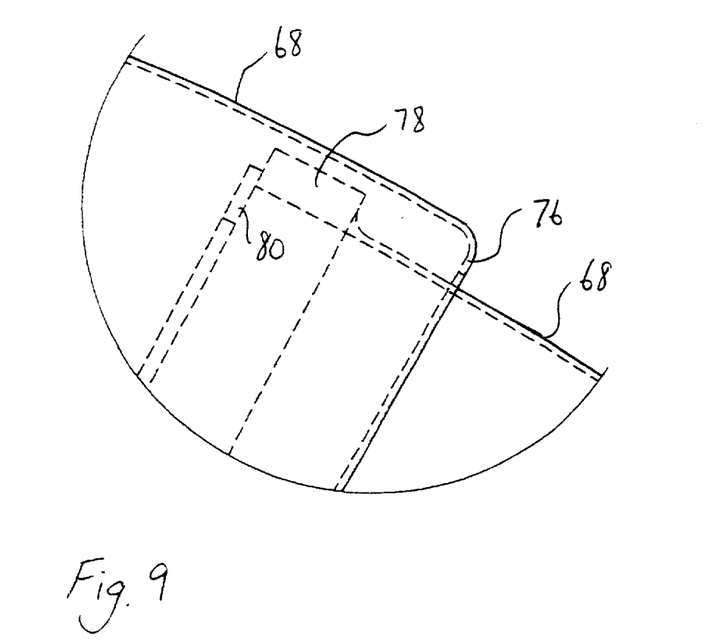
FIG. 9 shows a diagrammatic side view on an enlarged scale of portions of the cover shown in FIGS. 5 and 6 in a not quite fully extended position.

Each segment 68 is provided with an inwardly turned lip 76 around its forward edge, as shown in FIG. 9. Each segment 68 is also provided with an outwardly extending lip 78 around its rearward edge and also an inwardly turned lip 80 around its rearward edge adjacent to the outwardly turned lip 78.

The innermost segment 68 is fixed relative to the shaft 64.

Otherwise, the modification of the apparatus shown in FIGS. 5 to 9, especially as regards the passing of deodorising gas through the inlet 34 over the contents of the skip 10 is substantially as described with reference to FIGS. 1 to 4.

With the cover 69 in the retracted position, the motors 68 are energised to rotate the shaft 64 and with it the innermost segment 68 in a forward direction. When the outwardly turned lip 78 of the innermost segment 68 abuts the inwardly turned lip 76 of the adjacent segment, further rotation of the innermost segment 68 draws with it the adjacent segment so that this too is now rotated up and over the skip 10. The adjacent segment is then coupled to the next succeeding segment in the series in the same way, and ultimately the whole cover 69 is extended over the skip 10 with the innermost segment 68 having its forward edge now on the ground.

When the skip 10 is full and is ready for removal, the motors 68 are energised to lift the innermost segments 68 upwardly and rearwardly over the skip 10. When the lip 78 of the innermost segment 68 abuts the inwardly turned lip 80 of the adjacent segment, this in turn is lifted upwardly and rearwardly over the skip 10 by the action of the innermost segment 68. The adjacent segment 68 in its turn becomes coupled with the next succeeding segment of the series in substantially the same way, and ultimately the whole cover is retracted so that once again all the segments 68 are nestled one within the other in the manner indicated in FIGS. 7 and 8, thus providing access to the skip 10.

It is possible for the chute 26 to extend to a position above the cover 69 as shown in dotted lines in FIG. 5, in which case the segment 68 adjacent to the outlet from the chute 26 would be provided with an appropriate aperture.

Numerous modifications and variations to the illustrated embodiments may occur to the reader without taking the resulting construction outside the scope of the present invention. For example, a top generally horizontal mounting board 50 may be supported on the top of the backboard 18 by means of support brackets 52. The blower 30 with the ioniser 32 may be positioned on this top mounting board 50, which is provided with an inlet for this purpose, instead of on the backboard 18. The turn-buckles and Velcro (Trade Mark) may then be provided along a front edge 54 of the mounting wall 50, and turn-buckles and Velcro (Trade Mark) may also be provided along the front edge of each support bracket 52 and then downwardly along the back of the mounting board as shown in FIG. 3. In this instance, the incoming ionised air is dispersed over the top of the grit rather than being directly blown across it.

In the modification shown in FIGS. 5 to 9, the motors 68 may be replaced by levers to enable the conch to be operated manually.

The rigid material from which the segments 68 are made may comprise glass fibre, or sheet metal, or another suitable rigid sheet material.

We claim:

1. Odour control apparatus comprising a container for containing solid malodorous material, a cover configured to extend over the top of the container and create a barrier between the region immediately over the solid malodorous material and the surrounding air, and inlet means for feeding ionized air over the solid malodorous material contained in the container when the cover is extended over the top of the container.

2. Odour control apparatus according to claim 1, in which the cover comprises sheet material in the form of a plurality of segments to enable the cover to be extended over the container to cover it and retracted to provide access to the container.

3. Odour control apparatus according to claim 2, in which the segments overlap one another when the cover is retracted, and do not overlap one another, or overlap one another substantially less, when the cover is extended.

4. Odour control apparatus according to claim 3, in which the segments are provided with lips to act as abutment stops defining the limits to which adjacent segments can be moved relative to one another in the cover-extending direction.

5. Odour control apparatus according to claim 3, in which the segments are provided with lips to act as abutment stops defining the limits to which adjacent segments can be moved relative to one another in the cover-retracting direction.

6. Odour control apparatus according to claim 2, in which the cover is in the form of a conch.

7. Odour control apparatus according to claim 1, in which the cover comprises flexible sheet material.

8. Odour control apparatus according to claim 7, in which the sheet material is antistatic.

9. Odour control apparatus according to claim 7, in which the cover is water-resistant.

10. Odour control apparatus according to claim 7, in which the cover is air-breathable.

11. Odour control apparatus according to claim 7, in which the cover is provided with a drawable hem.

12. Odour control apparatus according to claim 7, in which the hem of the cover is elasticated.

13. Odor control apparatus according to claim 1, in which it further comprises support means to support at least a part of the cover.

14. Odour control apparatus according to claim 7, further comprising support means which support at least part of the cover in such a manner that it is slanted so that rainwater runs off it more easily than if it were horizontal.

15. Odour control apparatus according to claim 13, in which the said inlet means are provided in the said support means.

16. Odour control apparatus according to claim 13, in which the support means are provided with a chute to enable grit or other solid malodorous material to be fed into the container whilst the cover remains in place.

17. Odour control apparatus according to claim 13, in which the support means comprise a backboard.

18. Odour control apparatus according to claim 1, in which the container is in the form of a skip.

19. Odour control apparatus according to claim 1, wherein the cover comprises rigid sheet material in the form of a plurality of segments to enable the cover to be extended over an article to cover it and retracted to provide access to the article, in which the segments overlap one another when the cover is retracted and do not overlap one another, or overlap one another substantially less, when the cover is extended.

20. A method of treating solid malodorous material comprising placing the latter in a container, extending a cover over the top of the to create a banner between the regions immediately over the solid malodorous material surrounding air, and passing ionized air over the said malodorous material contained in the container when the cover is extended over the top of the container.

* * * * *